(12) United States Patent
Aunio et al.

(10) Patent No.: US 9,079,023 B2
(45) Date of Patent: Jul. 14, 2015

(54) PORTABLE DEVICE

(75) Inventors: Antti Aunio, Oulu (FI); Juuso Nissilä, Ii (FI)

(73) Assignee: VALKEE OY, Oulu (FI)

(*) Notice: Subject to any disclaimer, the term of this patent is extended or adjusted under 35 U.S.C. 154(b) by 1364 days.

(21) Appl. No.: 12/105,295

(22) Filed: Apr. 18, 2008

(65) Prior Publication Data

US 2008/0262575 A1  Oct. 23, 2008

(30) Foreign Application Priority Data

Apr. 18, 2007 (EP) .................................. 07106413

(51) Int. Cl.
*A61N 5/06* (2006.01)
*A61M 21/00* (2006.01)

(52) U.S. Cl.
CPC ............. *A61N 5/0618* (2013.01); *A61M 21/00* (2013.01); *A61M 2021/0044* (2013.01); *A61N 2005/0648* (2013.01)

(58) Field of Classification Search
USPC .............................. 600/318; 607/88, 89; 606/9
See application file for complete search history.

(56) References Cited

U.S. PATENT DOCUMENTS

| | | | |
|---|---|---|---|
| 5,470,846 A * | 11/1995 | Sandyk | 514/159 |
| 5,923,398 A | 7/1999 | Goldman | |
| 6,350,275 B1 * | 2/2002 | Vreman et al. | 607/88 |
| 2003/0056281 A1 | 3/2003 | Hasegawa | |
| 2005/0187597 A1 | 8/2005 | Vanderschuit | |
| 2006/0145457 A1 | 7/2006 | Prenzel et al. | |
| 2006/0217783 A1 * | 9/2006 | Harold | 607/53 |
| 2007/0002692 A1 * | 1/2007 | Van Brunt | 368/79 |
| 2007/0179563 A1 * | 8/2007 | Harold | 607/53 |
| 2008/0170476 A1 * | 7/2008 | Hurst | 368/250 |
| 2009/0018419 A1 * | 1/2009 | Torch | 600/318 |
| 2009/0058660 A1 * | 3/2009 | Torch | 340/573.1 |
| 2009/0105605 A1 * | 4/2009 | Abreu | 600/549 |

FOREIGN PATENT DOCUMENTS

| | | |
|---|---|---|
| DE | 6750962 | 1/1969 |
| DE | 102004058722 | 6/2006 |

OTHER PUBLICATIONS

Search report in corresponding European Application No. 07106413.

* cited by examiner

*Primary Examiner* — Ahmed M Farah
*Assistant Examiner* — Jeffrey Lipitz
(74) *Attorney, Agent, or Firm* — Young & Thompson

(57) ABSTRACT

A portable electronic device comprises illuminating unit (300) configured to illuminate extrapupillarily the skin covering a user's eye cavity with optical radiation, thus resulting in diffuse propagation of optical radiation energy to an optically sensitive tissue of the user's eye, and adapting unit (500, 510, 520, 530, 550, 560) for adapting the illuminating unit (300) to the user's head.

29 Claims, 4 Drawing Sheets

PORTABLE DEVICE

FIELD

The invention relates to portable devices providing human nerve tissue with optical stimulation.

BACKGROUND ART

Human nerve tissue includes regions which may be stimulated with optical radiation. Such stimulation may result in neural and/or metabolic response which may manifest itself as a difference in circadian rhythm, mental agility and/or abundance of hormones and physiological transmitters. A symptom associated with insufficient sunlight is known as SAD (Seasonal Affective Disorder).

The symptoms associated with insufficient sunlight may be reduced with artificial illumination installations which may be located in homes and/or working facilities. The artificial illumination installations are, however, large in size and are therefore virtually fixed to the operating environment. Furthermore, the artificial illumination installations require a large amount of power, and the efficiency is low.

Therefore it is useful to consider techniques for providing optically sensitive nerve tissue with optical stimulation.

BRIEF DESCRIPTION

An object of the invention is to provide a portable electronic device so as to provide the human nerve tissue with artificial illumination.

In an aspect, the invention provides a portable electronic device, comprising: illuminating means configured to illuminate extrapupillarily the skin covering a user's eye cavity with optical radiation, thus resulting in diffuse propagation of optical radiation energy to an optically sensitive tissue of the user's eye; and adapting means for adapting the illuminating means to the user's head.

The invention provides several advantages. The portability of the illumination device frees the user to enjoy illumination treatment anywhere. The extrapupillary optical illumination reduces the amount of glare due to optical illumination, thus enabling the user to perform virtually normally during an illumination session.

LIST OF DRAWINGS

Figure 1:
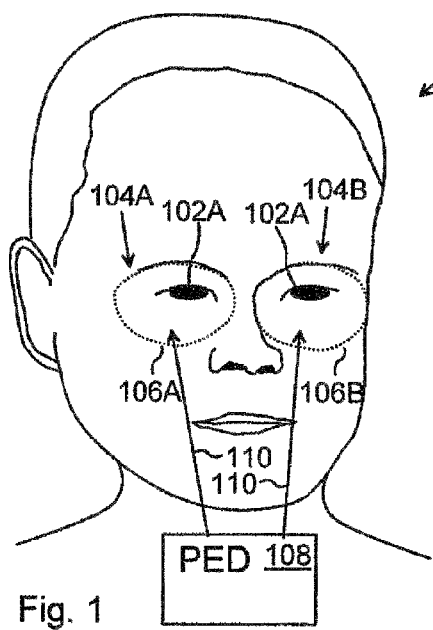
Figure 2:
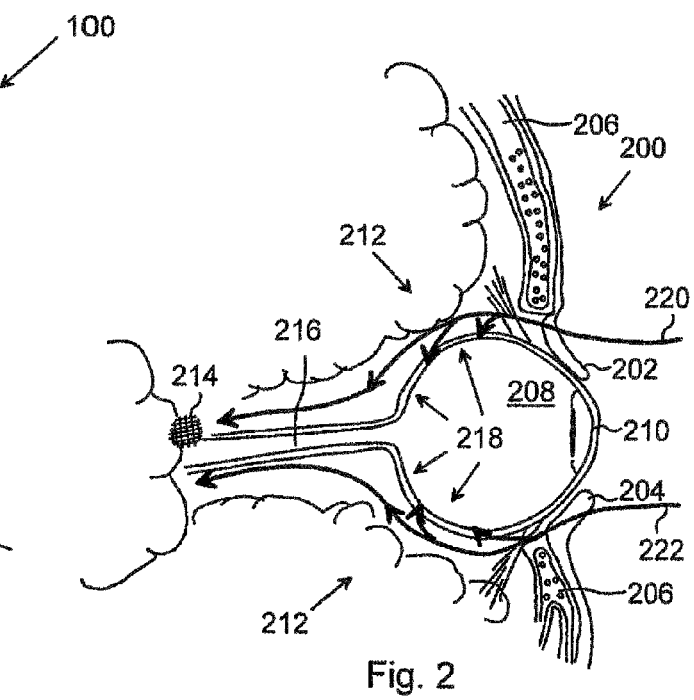
Figure 3:
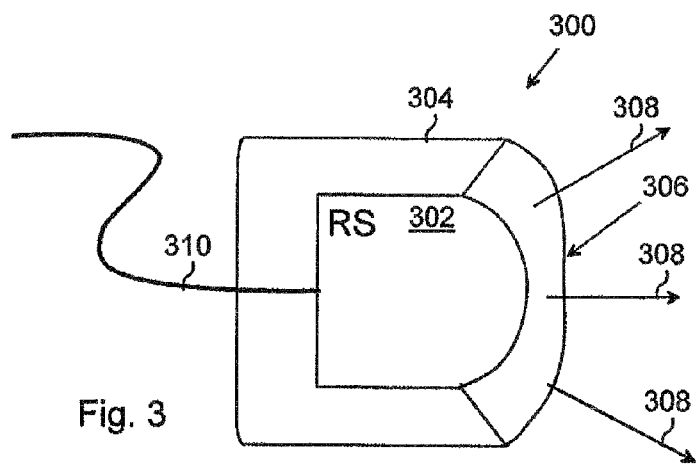
Figure 4:
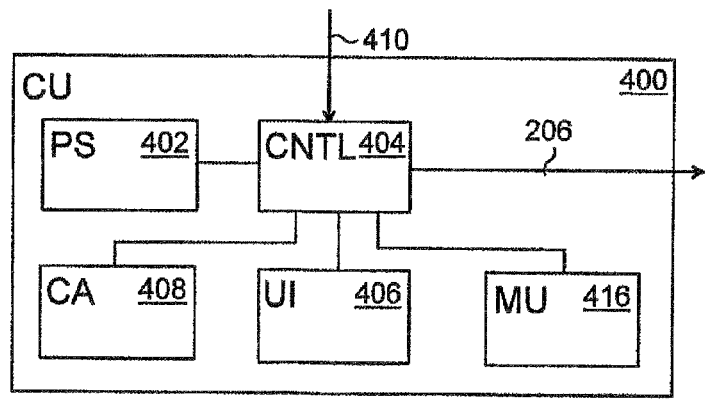
Figure 5:
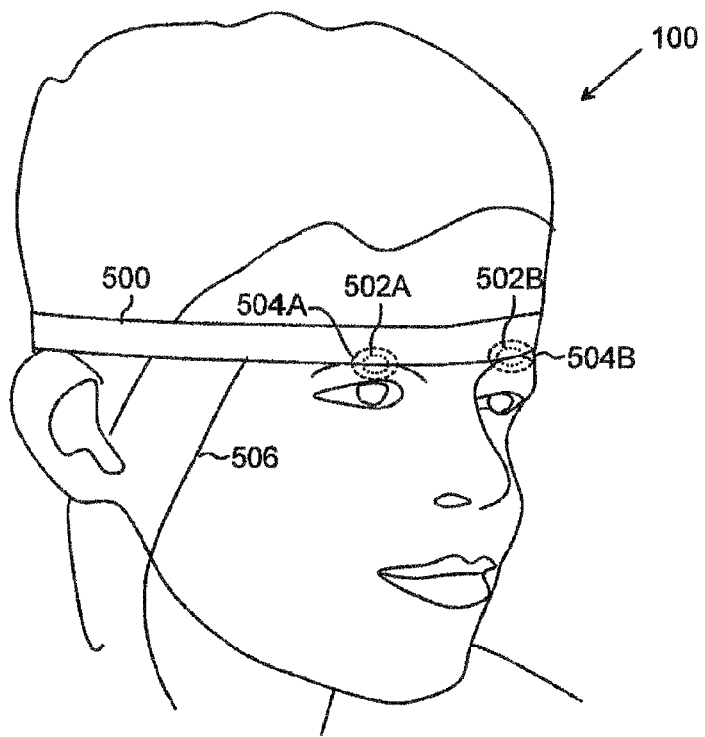
Figure 6:
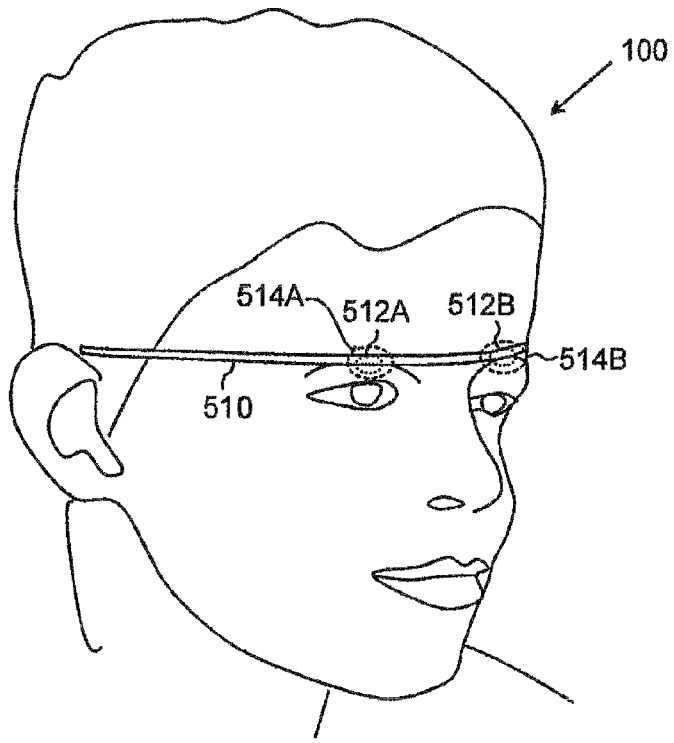
Figure 7:
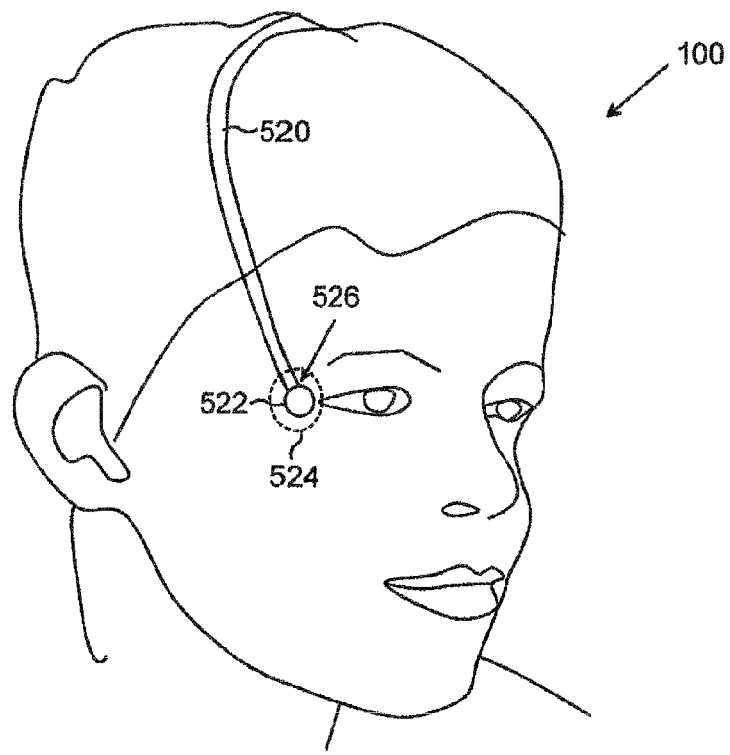
Figure 8:
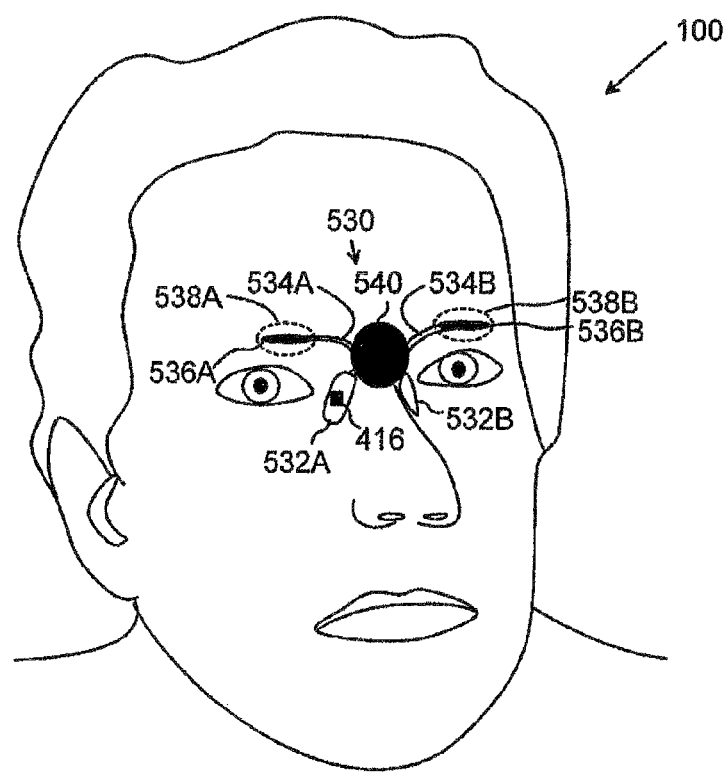
Figure 9:
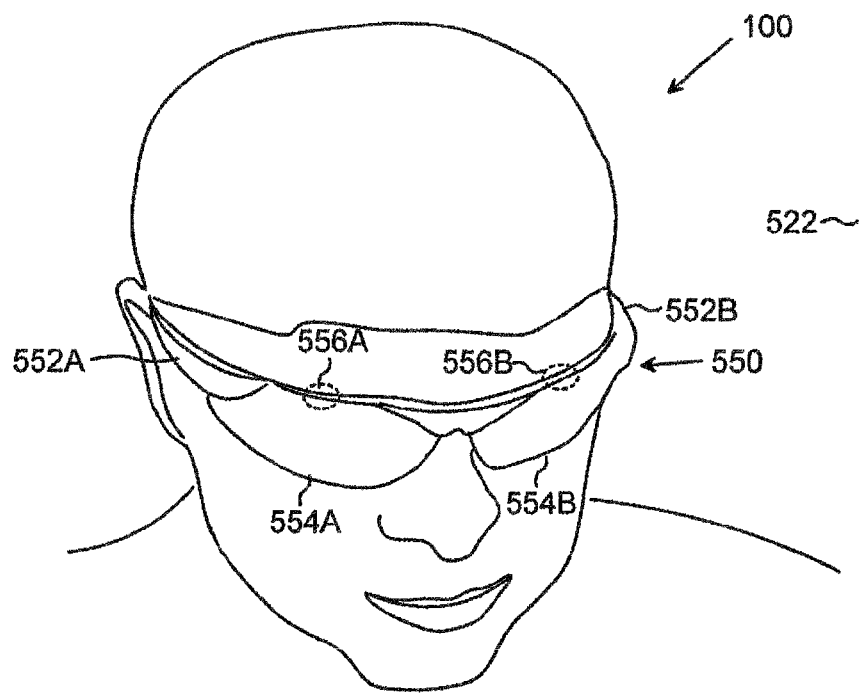
Figure 10:
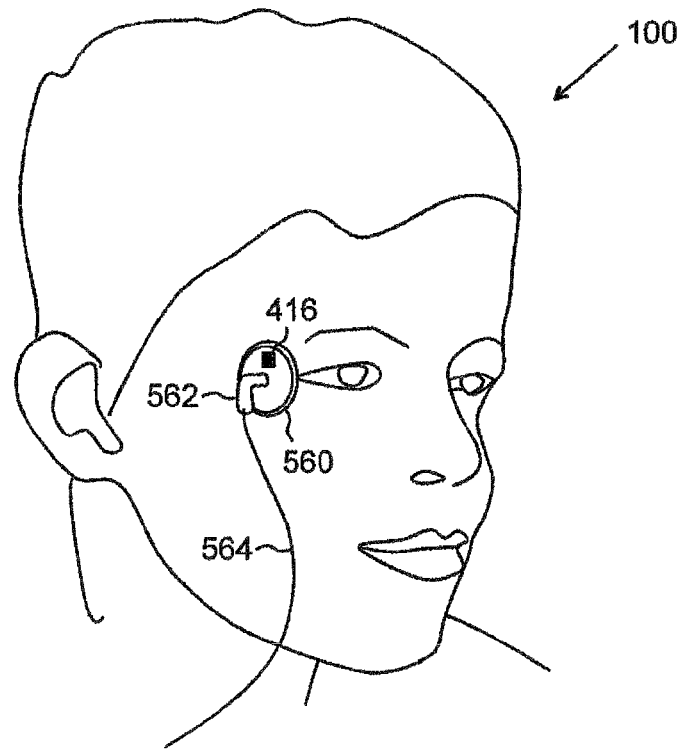

In the following, the invention will be described in greater detail with reference to the embodiments and the accompanying drawings, in which FIG. 1 shows a first embodiment of the invention;
FIG. 2 shows a propagation principle of optical radiation in a human head;
FIG. 3 shows an example of a radiation element;
FIG. 4 shows an example of a control unit;
FIG. 5 shows a second example of a portable electronic device;
FIG. 6 shows a third example of a portable electronic device;
FIG. 7 shows a fourth example of a portable electronic device;
FIG. 8 shows a fifth example of a portable electronic device;
FIG. 9 shows a sixth example of a portable electronic device;
FIG. 10 shows yet another example of a portable electronic device.

DESCRIPTION OF EMBODIMENTS

With reference to FIG. 1, the skin covering user's 100 eye cavity 104A, 104B is exposed extrapupillarily to optical radiation 110, also referred to as optical illumination 110, by a portable electronic device (PED) 108.

The user's 100 eye cavity 104A, 104B is typically confined by a cavity edge 106A, 106B which defines the opening to the eye cavity 104A, 104B.

The skin covering the eye cavity comprises the skin of the upper eye lid and that of the lower eye lid.

In extrapupillary optical illumination 110, the optical radiation 110 is aimed at parts of the eye 102A, 102B that are external to the pupil of the user's eye 102A, 102B. As a result, the optical radiation 110 is not intentionally projected to the user's 100 retina, and the optical stimulus sensed by the photoreceptors, such as cones and rods, is low. Thus, the user may sense optical stimuli from the environment during the optical illumination, and the user is able to perform normally during the exposure.

The portable electronic device 108 is portable in the sense that the user 100 is capable of carrying the portable electronic device 108 without externally supported appliances, such as trolleys.

In an embodiment of the invention, the portable electronic device 108 is further user-specific in the meaning that the person under exposure of optical radiation 110 also controls the portable electronic device 108. Control in this context means preparing the portable electronic device 108 for operation.

With reference to FIG. 2, a propagation mechanism of optical radiation energy is shown. FIG. 2 shows a user's eye 200, upper eye lid 202, lower eye lid 204, bone tissue 206, eyeball 208, pupil 210, brain tissue 212, suprachiasmatic nucleus (SCN) 214, retinohypothalamic tract 216 and retina 218.

The bone tissue 206 defines the cavity edge 106A, 106B shown in FIG. 1.

In an embodiment of the invention, the skin of the upper eye lid 202 is exposed to optical radiation 220 which penetrates into the skin and enters the bone and soft tissue around the eye. A portion of the optical radiation energy penetrates into the retina 218 and reaches the photosensitive ganglion cells. A portion of the radiation energy propagates to the back of the eyeball 208 and may reach the suprachiasmatic nucleus 214 and the retinohypothalamic tract 216.

In an embodiment of the invention, the skin of the lower eye lid 204 is exposed to optical radiation 222 which penetrates into the skin and enters the soft tissue surrounding the eyeball 208. The propagation mechanism is similar to that when the upper eyelid 202 is exposed to the optical radiation 220. The propagation of the optical radiation is based on diffusion of the optical radiation in the soft tissue. One propagation mechanism may be diffusion of the optical radiation along the surface of the eyeball 208, also referred to as the sclera.

It is believed that the physiological effect of the optical radiation energy is based on stimuli of photosensitive ganglion cells, also referred to as melanopsin-containing ganglion cells, which are located in the retina 218. The photosensitive ganglion cells are believed to play an important role in the synchronizing circadian rhythm to the artificial and ambient illumination. The photosensitive ganglion cells are intrinsically photosensitive, meaning that they are excited by the optical radiation 220, 222 even when no influences from classical photoreceptors, such as rods and cones, are present.

The suprachiasmatic nucleus 214 is a region of the brain, located in the hypothalamus, that is responsible for controlling the circadian rhythms. The suprachiasmatic nucleus 214 receives inputs from the photosensitive ganglion cells cells via the retinohypothalamic tract 216.

The optical sensation of the photosensitive ganglion cells is based on extrapupillary optical illumination, where the optical radiation 220, 222 is conducted from the user's skin to the ganglion layer via the soft tissue located in the user's eye cavity 104A, 104B.

The propagation mechanism and the illumination of the extrapupillary portion of the eye results in the stimulation level of the photoreceptors, such as cones and rods, being low by the illumination, and the user senses no glare due to the optical illumination. Thus, the user 100 is capable of performing virtually normally during an illumination session. When the eyelids are closed, a soft dim light reach the retina 218 through the pupils.

With reference to FIG. 3, an example of a radiation element 300 comprises a radiation source (RS) 302 and a shield 304.

The shield 304 may comprise an optically transparent part 306 which acts as a medium for the optical radiation 308. The optically transparent part 306 may comprise focusing characteristics such that the optical radiation may be aimed at the user's skin pointwisely. The optical transparent part 306 may be made from optically transparent glass or plastic, or the optical transparent part 306 may be filled with air.

In an embodiment of the invention, the transparent part 306 acts as an optical adapter between the radiation source 302 and the user's skin. The optical adapter may be shaped so as to enable the radiation element 300 to be brought into contact with the user's skin, thus maximizing the efficiency of the optical illumination and reducing the amount of power required by the radiation source 302.

The radiation source 302 is an electro-optic component which transforms electric power 310 into optical radiation 308. The radiation source 302 may comprise, for example, a light emitting diode (LED), a diode laser, or a conventional black body radiator.

The radiation source 302 may comprise a plurality of spectral sources, each of which having characteristic spectral or spatial distribution.

In an embodiment of the invention, the spectral distribution may be controlled. The radiation source may comprise an RGB LED, for example, where each LED may be controlled separately so that that the desired spectral distribution is obtained.

With reference to FIG. 4, an example of a control unit (CU) 400 comprises a power source (PS), a controller (CNTL) and a user interface (UI) 406. The control unit 400 may be coupled to the radiation element 300 of FIG. 2. A task of the control unit 400 is to control the optical illumination provided by the radiation element 300.

The power source 402 supplies electric power to the controller 404. The power source 402 may comprise a battery or a transformer. The power source may comprise a switching regulator for generating high DC (Direct Current) voltage from low DC voltage supplied by a battery, for example. The switching regulator enables low-voltage batteries to be used and the control voltage of LEDs to be adjusted. An adjustment of the control voltage may be used for obtaining a threshold voltage of the LEDs and the optimum current for the LEDs. In an embodiment of the invention, the switching regulator is integrated into the controller 404.

The controller 404 may comprise power control means, such as transistors and/or switches, for controlling the electric power 310.

In an embodiment of the invention, the controller comprises a digital processor and memory.

The memory may include a computer program of coded instructions on the basis of which the digital processor may generate control commands for the power control means. The controller 404 may also be implemented with ASIC (Application-Specific Integrated Circuit).

The controller 404 may further comprise control logic for recharging the battery and for monitoring the charge status of the battery.

In an embodiment of the invention, the controller 404 controls the temporal distribution of the optical illumination. The temporal distribution aims at providing the user with an appropriate dosage of optical radiation.

The temporal distribution may comprise short periods, for example of the order of seconds, in order to control the short-term optical radiation power.

The temporal distribution may comprise long periods, for example of the order of minutes, hours or days, in order to control the long-term optical radiation power. The long periods may comprise time sequences during which the optical illumination is provided.

The temporal distribution may be generated by modulating the electric power 310 temporally. The modulation may be discrete, thus resulting in on and off states of the electric power 308.

In an embodiment of the invention, the modulation is continuous, thus resulting virtually in any power of the optical radiation 310 between appropriate limits.

In an embodiment of the invention, the controller 404 controls the spectral distribution of the optical radiation 308. The spectral distribution may be controlled by directing desired electric power 310 to each spectral source.

The controller 404 may include logic for implementing several illumination programs, each of the illumination programs comprising specific temporal and spectral distribution. The illumination programs may be provided for achieving following effects:
  shift of the circadian rhythm
  treatment of jet lag
  treatment of dyssomnia due to shift work
  treatment of season affective disorder and other mental disorders
  treatment of neural deficiency due to decreased light sensitivity of the brain
  easing waking up
  treatment of stress symptoms
  improvement of the plasticity of the brain
  treatment of sexual insufficiency With further reference to FIG. 4, the control unit 300 may comprise a communication adapter (CA) 408 for coupling the portable electronic device 108 to an external control device, such as a mobile phone, a PDA (Personal Digital Assistant), a personal computer, a laptop or a music player. The communication adapter 408 may implement a wireless interface, such as that based on IrDA (Infrared Data Association), BlueTooth, ZigBee and/or BlueLite (BlueTooth Lite).

In an embodiment of the invention, the communication adapter 408 implements a communication interface based on an induction loop, USB (Universal Serial Bus) and/or an audio visual interface.

The communication adapter 408 may receive a command from the external control device and forward the command to the controller 404.

The controller receives the command and controls the electric power 310 accordingly.

The communication adapter 408 enables a user interface of the external control device to be used when the portable electronic device is operated. The communication adapter 408 further enables control logic to be situated into the external control device.

The user interface 406 may comprise a keypad, a keyboard, and a display device, such as an LCD (Liquid Crystal Display). The user interface 406 may provide the user 100 with a switching capability for switching the portable electronic device 108 on and off. Furthermore, the user interface 406 may be configured to show the state of the portable electronic device 108 to the user 100.

Some parts, such as parts of the keypad, may be implemented as a separate unit located in the proximity of the radiation element 300. The control unit 400 may be connected to the radiation element 300 over a wire. In such a case, a separate keypad provides the user with easier access to the user interface 406.

In an embodiment of the invention, the controller 404 includes coded instructions for providing the user 100 with medical instructions for taking medicine or other chemical substances. The medical instructions may comprise the specification of the medicine or chemical substance and/or the timing of the intake of the medicine or chemical substance. The medicine or chemical substance may or may not have a synergism with optical radiation 108, 308. The medicine or chemical substance may improve the physiological response of the nerve tissue to the optical radiation 108, 308.

In an embodiment of the invention, the portable electronic device 108 comprises a recharging interface for receiving electric power for recharging the power source 402.

The portable electronic device 108 may further include a measurement unit (MU) 416 which measures a physiological parameter from the user's 100 body. A physiological parameter may characterize body temperature, activity or heart rate or a heart rate variable.

The measurement unit 416 may supply measurement information to the controller 404 which performs control operations accordingly.

In an embodiment of the invention, the measurement unit 416 measures movement of the eye of the user 100. The portable electronic device 108 may comprise a detector, such as a mechanical or optical movement sensing detector, for detecting eye movement of the user 100. The eye movement typically indicates user activity. The controller 404 may regulate the dosage of the optical radiation 108, 308 on the basis of the user activity. If the measurement indicates decreased activity, the dosage of the optical radiation may be increased and vice versa. Eye movements can be detected by electromagnetic measurements due to the dipole nature of the human eyeball.

In an embodiment of the invention, the control unit 400 is integrated into an audio player. The control unit 400 and the audio player may use shared resources, such as digital signal processing resources, memory resources, and the power source.

In an embodiment of the invention, the controller 404 receives measurement information 410 generated in an external measurement system, such as a heart rate measuring system. The controller 404 may regulate the spectral and/or temporal characteristics of the optical radiation 108, 308 on the basis of the measurement information 410. The measurement information 410 may be transferred via an adapter similar to the communication adapter 408.

The measurement information 410 may characterize the user's 100 physiological state before treatment with optical radiation 108, 308. The controller 404 may select the distribution of the optical radiation 108, 308 automatically so as to comply with the user's current physiological state.

In an embodiment of the invention, the measurement information 410 characterizes the user's response to the treatment with the optical radiation 108, 308. The controller 404 may thus implement a physiological feedback mechanism, where the distribution of the optical radiation 108, 308 depends on the user's current physiological state.

In an embodiment of the invention, the measurement information 410 characterizes the user's snoring. In this case, the measurement information 410 may include the temporal variation and intensity of the snoring.

In an embodiment of the invention, the measurement information 410 comprises the user's heart rate information, such as heart rate and/or heart rate variability. In this case, the measurement information 410 may be generated in a portable heart rate monitor.

In an embodiment of the invention, the measurement information comprises the user's blood pressure information.

In an embodiment of the invention, the measurement information 410 comprises the user's blood oxygen saturation.

In an embodiment of the invention, the measurement information 410 comprises the user's blood glucose level.

In an embodiment of the invention, the measurement information 410 comprises the user's electroencephalogram (EEG).

In an embodiment of the invention, the measurement information 410 comprises the user's skin conductivity.

In an embodiment of the invention, the measurement information 410 comprises the user's breath frequency.

In an embodiment of the invention, the measurement information 410 comprises the user's eye movements.

In an embodiment of the invention, the measurement information 410 comprises the user's eye lid opening and closing characteristics which indicate the state of sleepiness.

In an embodiment of the invention, the measurement information 410 comprises information on body core and/or skin temperature.

In an embodiment of the invention, the measurement information 410 comprises the user's limb activity.

The control unit 400 may be implemented with a computer program, digital processor and memory. Furthermore, some functionalities may be implemented with ASIC and/or FPGA (Field Programmable Gate Array).

In an embodiment of the invention, the control unit 400 and the radiation element 300 form an integrated structure. In an integrated structure, the control unit 400 and the radiation element 300 share the same housing.

In an embodiment of the invention, the control unit 400 and the radiation element 300 are connected by a wire.

With reference to FIG. 5, the portable electric device 108 may comprise a band-like supporting structure 500 which extends at least partially around the user's 100 head. The band-like supporting structure 500 may comprise an elastic body so as to flexibly attach the portable electric device around the user's 100 head.

The band-like supporting structure 500 may be designed to be attached to the user's 100 forehead region. Radiation elements 504A, 504B may be fixed to the lower part of the band-like supporting structure 500 and located so that the user's upper lid regions 504A, 504B are illuminated. The upper lid region extends to the eyebrow region which is typically located at the edge of the eye cavity. The control unit 400 may be fixed to the band-like supporting structure 500, or the control unit 400 may be a separate unit coupled by a wire 506 to the radiation elements 504A, 504B.

With reference to FIG. 6, a band-like supporting structure 510 may be made from a semi-rigid material, and the attachment between the user's head and the band-like supporting structure 510 is based on the rigidity of the band-like supporting structure 510. The band-like supporting structure 510 may be made from plastic or metal, for example. Radiation elements 512A, 512B may be arranged in the inner circumference of the band-like supporting structure 510 and configured to illuminate the user's upper lid regions 514A, 514B.

With reference to the example of FIG. 7, a band-like supporting structure 520 comprises open ends 526. In this case, the band-like supporting structure 520 is made of a semi-rigid material, such as plastic or metal. A radiation element 522 is attached to an open end 526. In this case, the illumination area 524 resides in the side of the eye.

With reference to FIG. 8, in an embodiment of the invention, a portable electronic device 530 comprises a nose adapter for supporting the portable electronic device 530 against the user's nose.

The nose adapter may comprise a nose bridge and nose pads 532A, 532B attached to the nose bridge. The nose adapter may further comprise arms 534A, 534B which extend from the nose bridge to the upper part of the user's upper lids. Radiation elements 536A, 536B may be located in the arms 534A, 534B and be brought into the proximity of or be in contact with the skin of the upper lids. In this case the illumination is aimed at the user's 100 upper lid area 538A, 538B. In this case the illumination area may be of the order of few millimeters, which corresponds to point-wise optical illumination.

In an embodiment of the invention, radiation elements 536A, 536B, such as diodes, are carried by the nose pads 532A, 532B. In an embodiment of the invention, the radiation elements 536A, 536B are integrated into the nose pads 532A, 532B.

A control unit 540 may be an integral part of the nose adapter. Therefore, the portable electronic device 530 in this embodiment provides a compact unit which is easy to install to and remove from the user's head.

FIG. 9 shows an embodiment, where radiation elements 556A, 556B are integrated into eyewear 550, such as eyeglasses or sunglasses. The radiation elements may be located in the eyewear as to illuminate the upper lid regions, lower lid regions or other regions at the opening of the eye cavity. In an embodiment of the invention, radiation elements 536A, 536B, such as diodes, are carried by the nose pads of the eyewear 550. In an embodiment of the invention, the radiation elements 536A, 536B are integrated into the nose pads of the eyewear 550.

The eyewear 550 typically comprises a nose bridge, optical elements 554A, 554B, such as lenses, and paddles 552A, 552B which extend behind the user's ears. The control unit 400 may be integrated into the eye-wear 550 in a manner similar to that in FIG. 8, or the control unit 400 may be a separate unit wired with the eyewear 550.

In an embodiment of the invention, the measurement unit 416 is integrated into a nose pad 532A, 532B.

With reference to FIG. 10, a radiation element 562 may be integrated into an adhesive member 560 which attaches the radiation element 562 to the user's 100 skin on the basis of adhesion between the adhesive member 560 and the user's 100 skin. The radiation element 562 may be coupled to the control unit 400 by a wire 564. In an embodiment of the invention, the control unit 400 is integrated into a radiation element 562 so as to provide a compact portable electronic device.

In an embodiment of the invention, the adhesive member 560 comprises a measurement unit 416 which may detect eye movements, for example.

The adhesive element 562 typically comprises an adhesive contact surface which may be replaceable.

Even though the invention has been described above with reference to an example according to the accompanying drawings, it is clear that the invention is not restricted thereto but it can be modified in several ways within the scope of the appended claims.

The invention claimed is:

1. A portable electronic device, comprising:
   one or more LED light sources configured for physical contact with a user's skin; and
   a connecting structure configured to be mounted on a head of the user, the one or more LED light sources attached to the connecting structure such that, when the connecting structure is worn on the head, the one or more LED light sources are positioned and maintained by the connecting structure in contact with a skin of an eyelid of the user at a position outside an area of the pupil of the user's eye,
   the one or more LED light sources positioned outside of an area in front of a pupil of a user's eye so that the optical radiation emitted from the one or more LED light sources diffusely propagates through soft tissue behind the eyelid toward a suprachiasmatic nucleus of the user behind the eye of the user, said one or more LED light sources oriented so that said optical radiation does not impinge upon the pupil of the user.

2. The portable electronic device of claim 1, wherein the connecting structure comprises a band-like supporting structure configured to extend at least partially around the user's head.

3. The portable electronic device of claim 2,
   wherein the band-like supporting structure comprises open ends; and
   wherein the one or more LED light sources are attached to at least one of the open ends and positioned such that, when worn by the user, the one or more LED light sources contact the skin on the eyelid at a position above a level of the pupil.

4. The portable electronic device of claim 1, wherein the connecting structure comprises a nose adapter configured to be mounted on a nose of the user.

5. The portable electronic device of claim 4, wherein the nose adapter further comprises an arm configured to extend from a bridge of the user's nose to an upper lid area of the user's eye above a level of the pupil, the one or more LED light sources being connected to the arm, and the arm positioned so that the one or more LED light sources are in contact with a skin of the user at the upper lid area.

6. The portable electronic device of claim 4,
   wherein the nose adapter comprises nose pads; and
   wherein the one or more LED light sources are integrated into the nose pads.

7. The portable electronic device of claim 1, wherein the connecting structure is in the form of an eyewear frame configured to rest in front of the user's eyes and comprising paddles configured to extend behind the user's ears for holding the eyewear frame in place on the head of the user.

8. The portable electronic device according to claim 7, wherein the eyewear frame includes a lens positioned in front of the eye of the user.

9. The portable electronic device of claim 1,
wherein the connecting structure comprises an adhesive element sufficient for attaching the one or more LED light sources to the user's skin, and
wherein the one or more LED light sources are integrated into the adhesive element.

10. The portable electronic device of claim 1, further comprising:
a control unit coupled to the one or more LED light sources and configured to control the one or more LED light sources.

11. The portable electronic device of claim 10, further comprising:
a measurement unit connected to the control unit and configured to measure a physiological parameter from the user's body and to supply measurement information to the control unit.

12. The portable electronic device of claim 11,
wherein the connecting structure comprises nose pads, and
wherein the measurement unit is integrated into the nose pads.

13. The portable electronic device of claim 10, wherein the connecting structure comprises an adhesive element which comprises a measurement unit configured to measure a physiological parameter from the user's body and supply measurement information to the control unit.

14. The portable electronic device of claim 10, wherein the one or more LED light sources and the control unit are an integrated structure.

15. The portable electronic device of claim 10,
wherein said control unit comprises a controller that implements plural illumination programs that are related to two or more of the group consisting of: shift of circadian rhythm, treatment of jet lag, treatment of dyssomnia due to shift work, treatment of season affective disorder and other mental disorders, treatment of neural deficiency due to decreased light sensitivity of the brain, easing of waking up, treatment of stress symptoms, improvement of plasticity of the brain, and treatment of sexual insufficiency.

16. The portable electronic device of claim 10, wherein said control unit comprises a controller that comprises coded instructions for providing the user with medical instructions for taking medicine or other chemical substances.

17. The portable electronic device according to claim 1, further comprising:
a communication interface configured to establish electronic communication with any of the group consisting of: a mobile phone, a PDA (Personal Digital Assistant) and a music player.

18. The portable electronic device according to claim 17, further comprising:
a control unit coupled to the one or more LED light sources and configured to control the one or more LED light sources, the communication interface being in electronic communication with the control unit.

19. The portable electronic device according to claim 1, further comprising:
a communication interface configured to establish electronic communication with a personal computer.

20. The portable electronic device according to claim 1, further comprising:
a control unit coupled to the one or more LED light sources and configured to control the one or more LED light sources, said control unit being integrated into an audio player.

21. The portable electronic device according to claim 20, wherein the control unit and the audio player are configured to use shared resources, the shared resources being one or more of the following resources: digital signal processing resources, memory resources, the power source.

22. The portable electronic device according to claim 1, further comprising: a controller for implementing a plurality of illumination programs, each of the illumination programs configured to cause the one or more LED light sources to emit a respective predetermined temporal and spectral distribution.

23. A portable electronic device, comprising:
one or more light sources configured for physical contact with a user's skin; and
a connecting structure configured to be mounted on a head of the user,
the one or more light sources attached to the connecting structure such that, when the connecting structure is worn on the head of the user, the one or more light sources are positioned and maintained by the connecting structure in contact with a skin on an eyelid of the user at a position outside a perimeter of an area in front of a pupil of the user's eye beneath the eyelid, so that optical radiation of the one or more light sources does not impinge upon said pupil,
all of the one or more light sources being positioned on the connecting structure to emit the optical radiation directly into the user's skin at one or more points of contact of the one or more light sources on the user's skin such that the optical radiation emitted from the one or more light sources diffusely propagates through soft tissue behind the eyelid toward a suprachiasmatic nucleus of the user behind the eye of the user.

24. The portable electronic device of claim 23, wherein the connecting structure comprises a band-like structure configured to fit at least partially around a forehead of the user.

25. The portable electronic device of claim 24,
wherein the band-like structure comprises an open end; and
wherein the one or more light sources are attached to the open end, and the open is configured such that, when the band-like structure is worn by the user, the one or more light sources contact the skin on the eyelid at a location above a level of the pupil.

26. The portable electronic device of claim 23, wherein the connecting structure comprises a nose adapter configured to be mounted on a nose of the user.

27. The portable electronic device of claim 26, wherein the nose adapter further comprises an arm configured to extend from a bridge of the user's nose to an upper lid area of the user's eye above a level of the pupil, at least one of the one or more light sources being connected to the arm, and the arm configured such that the at least one of the one or more light sources is in contact with a skin of the user at the upper lid area.

28. The portable electronic device of claim 23, wherein the connecting structure is free of light sources that emit optical radiation into the pupil of the user's eye.

29. The portable electronic device of claim 28, wherein the connecting structure comprises a two opposite end sections joined by a middle section, the two opposite end sections configured to extend at least partially around opposite sides of the head of the user with the middle section extending over the forehead of the user, the one or more light sources positioned on the middle section for contacting the skin of one or both eyelids of the user.

* * * * *